United States Patent [19]

Iwatschenko

[11] Patent Number: 4,775,368

[45] Date of Patent: Oct. 4, 1988

[54] INFUSION DEVICE

[75] Inventor: Peter Iwatschenko, Neunkirchen, Fed. Rep. of Germany

[73] Assignee: Pfrimmer-Viggo GmbH & Co. KG, Erlangen, Fed. Rep. of Germany

[21] Appl. No.: 14,679

[22] Filed: Feb. 13, 1987

[30] Foreign Application Priority Data

Feb. 19, 1986 [DE] Fed. Rep. of Germany ....... 3605319

[51] Int. Cl.⁴ ............................................ A61M 5/165
[52] U.S. Cl. ...................................... 604/253; 604/65; 128/DIG. 13
[58] Field of Search .................. 604/34, 65, 67, 245, 604/251, 253, 254, 171; 128/DIG. 13; 251/4

[56] References Cited

U.S. PATENT DOCUMENTS

| | | | |
|---|---|---|---|
| 2,807,012 | 9/1957 | Schwarz | 604/253 |
| 3,235,069 | 2/1966 | Bennett et al. | 604/171 |
| 3,479,001 | 11/1969 | Dower | 251/4 |
| 4,038,982 | 8/1977 | Burke et al. | 604/253 |
| 4,397,648 | 8/1983 | Knute | 604/253 |
| 4,493,710 | 1/1985 | King et al. | 604/253 |
| 4,496,351 | 1/1985 | Hillel et al. | 604/253 |
| 4,583,975 | 4/1986 | Pekkarinen et al. | 604/253 |
| 4,652,262 | 3/1987 | Ueracchi | 604/253 |
| 4,681,569 | 7/1987 | Coble et al. | 604/253 |

Primary Examiner—Stephen C. Pellegrino
Assistant Examiner—Ralph Lewis
Attorney, Agent, or Firm—Brumbaugh, Graves, Donohue & Raymond

[57] ABSTRACT

An infusion device is provided with an injection molded drip chamber, a drop sensor, such as a light barrier (26,28) or a piezoelectric crystal. An evaluation circuit processes the output signals furnished by the drop sensor and an optical display means (24) indicates the same to the operator. Recesses are formed integrally in or at the drip chamber to take up the drop sensor (26,28) the evaluation circuit, and the power source as this not only makes it possible to produce the infusion device at low cost but also permits the operator to have a look into the drip chamber, while the dripping rate is displayed optically at the same time. In a preferred modification there is complete control of the dripping rate by means of a control clamp (60) the flow cross section of which is adjustable by a drive means (64).

9 Claims, 6 Drawing Sheets

INFUSION DEVICE

BACKGROUND OF THE INVENTION

The instant invention relates to an infusion device having an injection molded drip chamber, a drop sensor, such as a light barrier or a piezoelectric member, an evaluation circuit for the output signals of the drop sensor, a power source, and a display means for optical display of an output signal provided by the evaluation circuit.

Infusion devices of the kind including a so-called drop counter are known, for example, from DE-GM No. 84 32 849, DE-GM No. 85 16 066, DE-OS No. 34 08 572, DE-OS No. 31 08 848, EP-OS No. 154 163, and DE-OS No. 34 03 969.

The object of infusion devices of the above mentioned type is to facilitate the adjustment of the dripping rate in gravity infusion. The operator (nurse) need not measure the instantaneous dripping rate in the drip chamber manually by a stop watch to adjust a control clamp. Instead, the dripping rate is measured automatically by a drop sensor, for example a light barrier or a piezoelectric member and indicated to the operator.

The rather high manufacturing costs of the known infusion devices with automatic measurement of the dripping rate and the optical display thereof is regarded as being a disadvantage. Therefore, the known measuring and display means were not offered as "disposable articles" (to be thrown away after single use), contrary to the drip chambers and hoses. Instead, they are intended for frequent and repetitive use.

Known infusion devices with electronic measurement of the dripping rate and display thereof furthermore have the disadvantage that the operator must rely on the dripping rate as indicated without having the possibility of looking into the drip chamber to see what is going on. Yet it is highly desirable that in spite of the automatic measuring and displaying the dripping rate, the operator is still able to get a full view of the drip chamber so that it can be verified by a simple glance at the instrument whether or not the resultant indicated measurement indicated makes sense.

It is an important aspect in the selling, shelfing, and stockkeeping of infusion devices which are mass-produced articles that the entire device can be handled as a compact unit. This is not possible if the drip chamber, the control clamp, and the hose on the one hand are provided as disposable articles, whereas the measuring and display means of the dripping rate are destined for multiple use (often to be used with different drip chambers, hoses, etc.).

It is, therefore, an object of the instant invention to devise an infusion device of the kind specified which can be produced as a compact unit at low cost. It is another object of the instant invention to provide an infusion device of the kind which will display the dripping rate electronically and also give the operator the opportunity of direct visual verification of the dripping condition inside the drip chamber.

SUMMARY OF THE INVENTION

To meet the above and further objects which will become apparent as the specification proceeds, it is provided, in accordance with the invention, that recesses are formed integrally in or at the drip chamber to receive at least the drop sensor, the evaluation circuit, the power source, and the display means.

Instead of providing a measuring and display instrument in a separate casing apart from the (disposable) drip chamber, the invention forms the drip chamber in the injection molding process such that all the structural members needed for measuring and displaying the dripping rate, such as the drop sensor, the power source, etc. can be inserted directly in recesses formed in the plastic material of the drip chamber. No separate (metal) casing is required to receive the electrical and optoelectrical components.

When making the drip chamber allowance can be made for the fact that it is to be furnished with measuring and display means of the dripping rate. For this reason a compact infusion device can be supplied which will be used once with a patient and then discarded.

A preferred modification of the invention provides that the recesses for taking up the power source, the evaluation circuit, and the display means are formed in the upper part of the drip chamber. This means that the major portion of the drip chamber, particularly its lower part remains free and can be looked into so that the operator can directly see the drops and the liquid level in the drip chamber and roughly check the measured result shown by the display means. The operator and the patient do not have to rely "blindly" on the proper functioning of the measuring means.

The recesses which take up the components mentioned preferably are provided in a reinforcement of the wall of the drip chamber which reinforcement is formed integrally and extends for a rather short part section of the overall length of the drip chamber. At either side of the drip chamber two diametrically opposed arms project from the reinforcement. In a preferred further development of the invention the transmitter and receiver of a light barrier are arranged at the ends of these arms. The light barrier which serves as drop sensor consequently hardly covers up the drip chamber, and it need not be assembled separately. In a preferred modification of the invention the power source used is a solar cell at the drip chamber.

It is obvious that the power supply of an infusion device according to the invention must be guaranteed over a long period of time. Therefore, a preferred modification of the invention provides for a protective cap covering the piercing tip of the drip chamber to interrupt the electrical connection between the power source and the loads in order not to waste current for operation of the drop sensor, the evaluation circuit, and/or the display means when these members are not in operation. When the operator takes the infusion device according to the invention out of its packing and before he or she punctures a rubber plug of the infusion flask by the piercing tip, first he or she will have to remove the protective cap so that the connection between the power source and the measuring and display means is not established until the infusion device is actually put into operation.

The electrical lines between the power source and the loads are laid in the wall of the drip chamber or in the thickened portion or reinforcement thereof.

In a preferred further development of the invention the measuring and display means provided at the drip chamber, as explained above, is coupled to a control clamp for the rate of flow of the infusion liquid through the infusion hose such that a complete control circuit is established. To this end the evaluation circuit of the measuring means of the dripping rate is connected to a drive means of the control clamp whereby the rate of flow through the hose acted upon by the control clamp is adjustable in response to an output signal of the evaluation circuit.

Also the infusion device to which a control clamp has been added still can be produced at low cost as a disposable unit.

BRIEF DESCRIPTION OF THE DRAWINGS

The invention will be described further, by way of example, with reference to the accompanying drawings, in which.

DESCRIPTION OF THE PREFERRED EMBODIMENT

Figure 1:
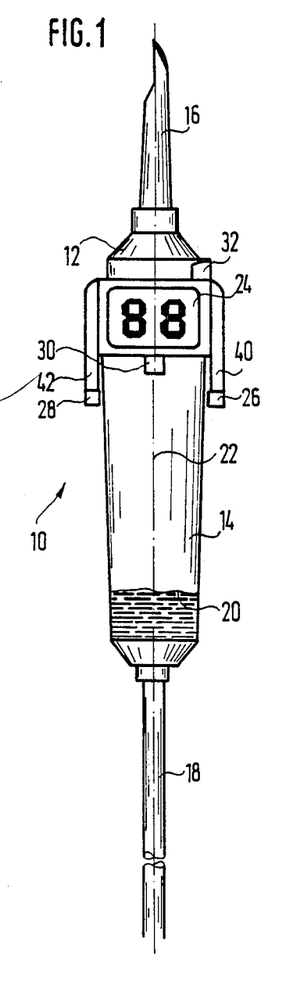
FIG. 1 is a diagrammatic presentation of a drip chamber with optical display of the dripping rate.
Figure 2:
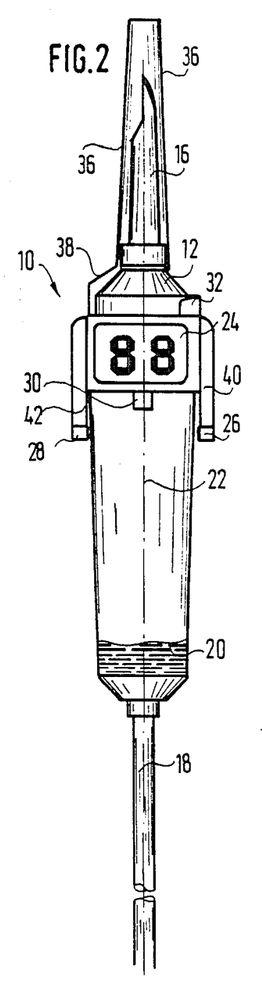
FIG. 2 shows the drip chamber according to FIG. 1, provided with a protective cap.
Figure 3:
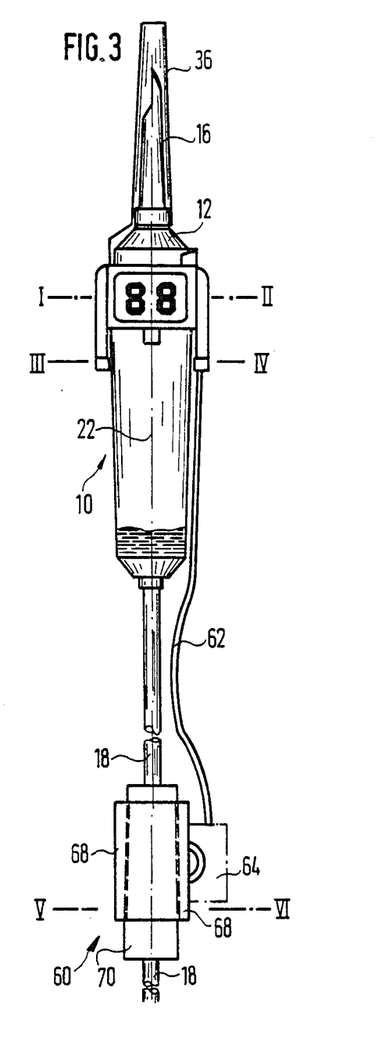
FIG. 3 shows the drip chamber according to FIGS. 1 and 2, including a control clamp.

As shown in FIG. 1, drip chamber 10 has an upper part 12 and a lower part 14 which are inserted one into the other coaxially. The upper part 12 of the drip chamber is provided with a piercing tip 16 adapted to be inserted into the rubber plug (not shown) of an infusion flask (not shown). For gravity infusion the drip chamber shown in FIGS. 1 to 3 is aligned vertically.

A hose 18 leads from drip chamber 10 to a patient (not shown). In the drip chamber 10 a liquid level 20 forms in accordance with the dripping rate adjusted. The drops fall out of a drop outlet 30 along the longitudinal axis 22 of the drip chamber down on to the liquid level 20.

An optical display means, such as a liquid crystal display (LCD) indicates the dripping rate measured to the operator.

Figure 4:
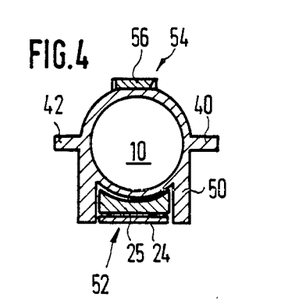
FIG. 4(a) is a sectional view taken along line I-II in FIG. 3.
FIG. 4(b) is an illustration of the circuit path in the infusion device when a cover member is engaged therewith.
FIG. 4(c) is an illustration of the circuit path in the infusion device when a cover has been removed.

An evaluation circuit 25 (FIGS. 4 and 6) integrated on a semiconductor substrate to be described in greater detail below is provided to determine the dripping rate. The dripping rate also is determined by a light barrier consisting of a light transmitter 26 and a light receiver 28, the drops falling out of the drop outlet 30 passing this light barrier.

In FIGS. 1 and 2 a fitting marked 32 is provided for an air filter so that atmospheric pressure will prevail in the interior of the drip chamber 10.

Figure 4B:
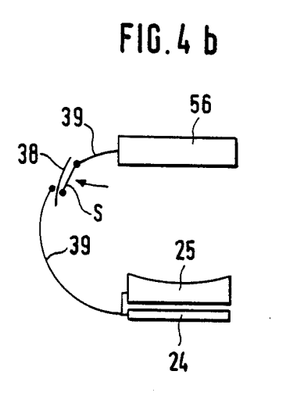
Figure 4C:
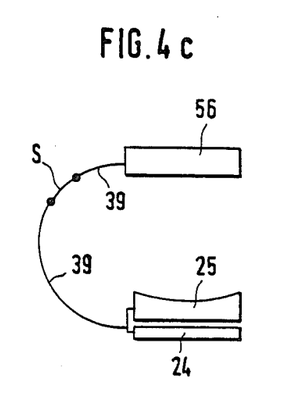

As shown in FIG. 2, the piercing tip 16 is covered by a transparent protective cap 36 which is provided at its lower end with an insulating disc 38 to separate the power source (FIG. 4(a)) from the loads, via switch S especially the evaluating circuit 25, the optical display means 24, and the light barrier composed of the transmitter 26 and receiver 28. It is only after the protective cap 36 and the insulating disc 38 have been removed by the operator that the power source is electrically connected to the loads mentioned (cf. line 39 in FIG. 6). As shown in FIGS. 4(b) and 4(c) the insulating disc 38 acts mechanically to keep switch A open when the cover is in place by nature of its disposition between the contacts of switch S, which is normally biased in the direction of the arrow. FIG. 4(c) shows the cover removed. The transmitter 26 and receiver 28 of the light barrier (drop sensor) are arranged at two arms 40, 42 extending in parallel with the longitudinal axis 22 of drip chamber 10 and diametrically opposed to each other.

As shown in FIG. 4, which presents a sectional view taken along line I-II in FIG. 3, the optical display means 24 and the evaluation circuit 25 are disposed in a reinforcement 50 of drip chamber 10. This reinforcement 50 is formed with a recess 54 for the display means 24 and the evaluation circuit 25. Another recess 54 is provided for the power source 56 which may be embodied by a solar cell or battery for example.

Figure 5:
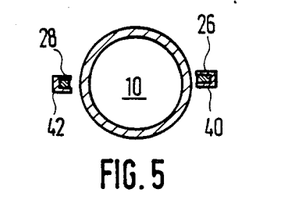
FIG. 5 is a sectional view taken along line III-IV in FIG. 3.

FIG. 5 is a sectional view taken along line III-IV in FIG. 3, including the drip chamber 10 and the light barrier composed of the transmitter 26 and receiver 28.

Figure 6:
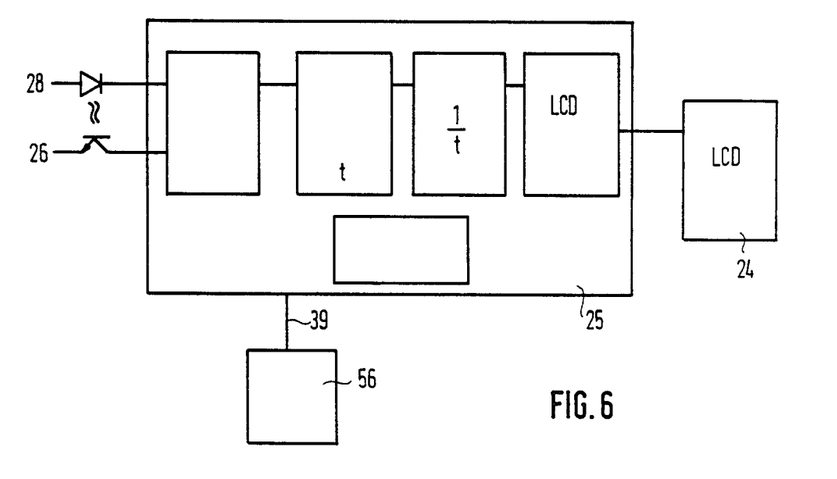
FIG. 6 is a block diagram of the evaluation circuit.

FIG. 6 is a block diagram of the evaluation circuit, including the power source 56 and the optical display means 24.

The signals furnished by the light barrier (transmitter 26, receiver 28) are introduced into a pulse shaper whose output signal is entered into a measuring circuit for the pulse separation t. The separation between measuring pulses corresponds to the interval between successive drops. The reciprocal value 1/t is the dripping rate. The dripping rate calculated is used to operate an LCD driver which is connected to the optical display means 24.

It is possible also to replace the light barrier composed of transmitter 26 and receiver 28 by a per se known piezo-electric crystal the pulses of which are entered into the pulse shaper.

FIG. 3 shows a control clamp 60 which is connected by a line 62 to the evaluation circuit 25. The control clamp 60 controls the flow cross section of the hose 18 in response to a desired value of the dripping rate. This makes it possible to balance pressure variations on the part of the patient so that the infusion speed will always conform to a constant theoretical value.

The control clamp 60 is provided with a drive means 64 (motor) which in turn is connected by line 62 to the evaluation circuit 25 from which it receives its control signals.

Figure 7:
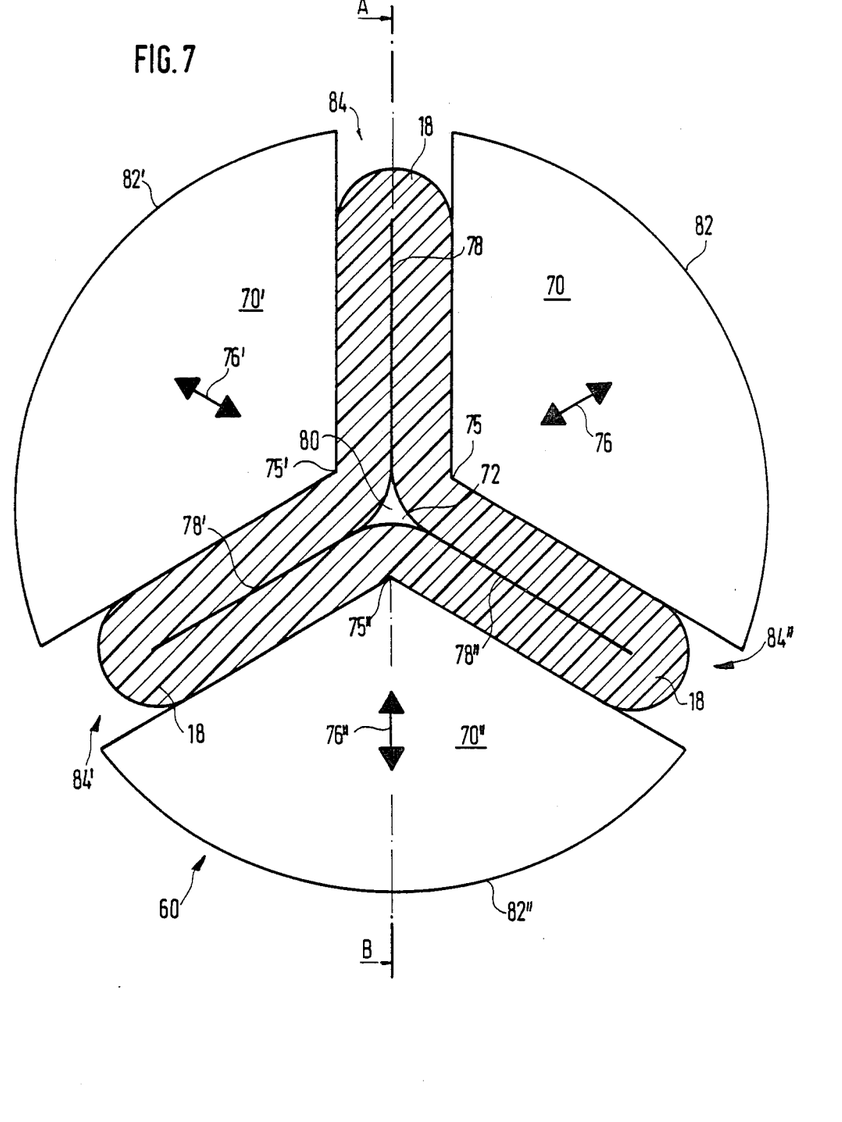
FIG. 7 is a sectional view of the control clamp taken along line V-VI in FIG. 3.
Figure 8:
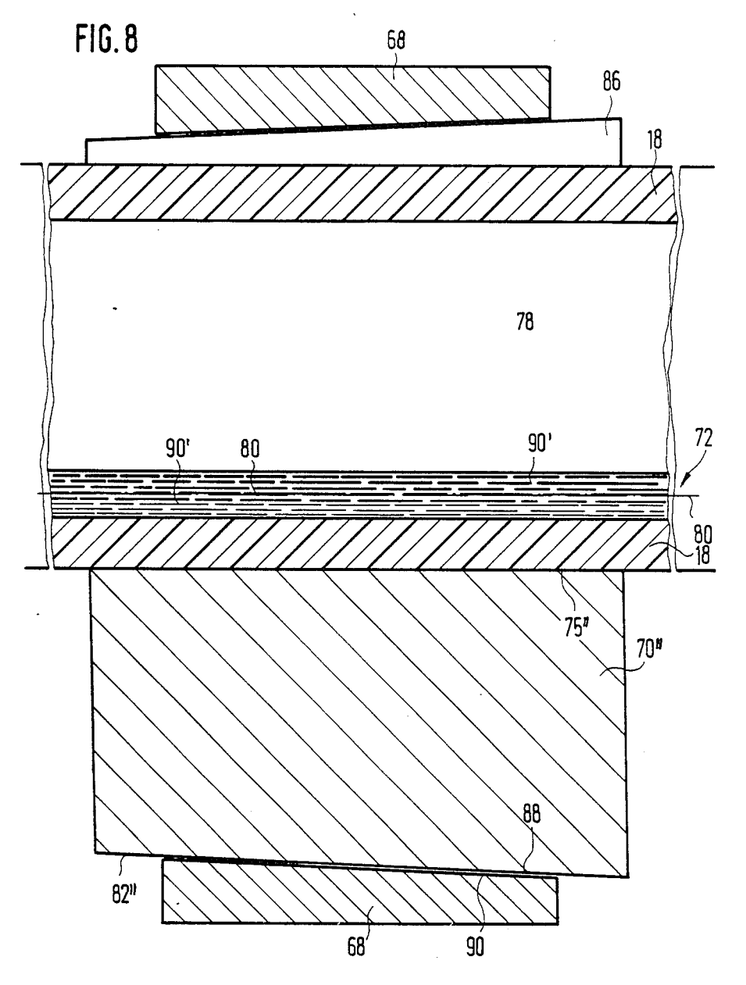
FIG. 8 is a sectional view taken along line A-B in FIG. 7.

Details of the control clamp 60 are shown in FIGS. 7 and 8.

According to FIG. 7 the hose 15 made of polyvinyl chloride (PVC) is squeezed together to flow cross section 72 by means of clamping jaws 70, 70', 70''. To this end the clamping jaws each are displaceable along a respective radius 76, 76', 76'' in the direction of the arrows shown. The central edges 75, 75', 75'' of the clamping jaws 70, 70', 70'' shaped like circular sectors move on radii 76, 76', 76'' so that the hose 18 is given a clamping state in rotational symmetry about its longitudinal axis 80. It may be gathered from FIG. 7, that the inner walls of the hose 18 come to lie closely against each other with their abutting surfaces 78, 78', 78'' practically becoming parallel planes so that the only remaining unobstructed space is the flow cross section 72 which is triangular in section and has concave side surfaces.

The peripheral portions 82, 82', 82" of the clamping jaws 70, 70', 70" form approximately a cylinder or cone. As shown in FIG. 7, spaces 84, 84', 84" remain free between the clamping jaws, and the hose 18 is partly clamped together in these respective spaces.

FIG. 8 is a sectional elevation along line A-B in FIG. 7. In addition to the components shown in FIG. 7 a centering insert 86 and an outer sleeve 68 are provided. The centering insert 86 is provided in the respective free spaces 84, 84', 84" between the clamping jaws and serves the purpose of squeezing sections of equal length of the hose 18 in the free spaces 84, 84', 84". At the outside, the centering inserts 86 together are flush with the peripheral portions 82, 82', 82" of the clamping jaws, supplementing the same at least approximately so as to form a full circle (not shown).

The centering insert, however, may be dispensed with if the hose 18 is preshaped at least in the range of the clamping jaws 70, 70', and 70" such that the edges 75, 75', 75" of the clamping jaws will positively engage the hose 18 in rotational symmetry at an angle of rotation of 120°. To this end, the hose 18 is preshaped plastically from the very beginning in the area of the control clamp to be approximately triangular in section. And it comprises three guide grooves (not shown) extending approximately parallel to the longitudinal axis 80 for engagement of the sharp edges 75, 75', 75" of the clamping jaws which enter in such manner than equal hose sections each are squeezed in the free spaces 84, 84', 84".

In the case of the embodiment shown in FIG. 8 the clamping jaws 70, 70', 70" are moved by means of sleeve 68 along radii 76, 76', 76" which pass through the longitudinal axis 80 of the hose 18. To accomplish that, the outer peripheral portions 82, 82', 82" of the clamping jaws are formed with an external thread 88 and the inner circumference of the sleeve 68 is formed with an internal thread 90. Thus the flow cross section 72 of hose 18 is varied in accordance with the status of threading between sleeve and clamping jaws, thereby controlling the flow velocity of the liquid 90'.

As shown in FIG. 8, the sharp edges 75, 75', 75" of the clamping jaws extend at least approximately parallel to the longitudinal axis 80 of the hose 18. Thus a relatively long hose section of some 2 to 5 cm can be clamped and the throttling of the flow velocity by means of the control clamp is characterized by good dampening. This means that any pressure variations at the end of the patient will be transmitted very much attenuated only to the other end of the control clamp so that the flow velocity does not differ at once from the desired value if there should be brief pressure variations at the end of the patient.

The drive means (electric motor 64) is fed by the power source 56 and controlled by the evaluation circuit 25 such that the dripping rate assumes a predetermined desired value. The drive means 64 thus rotates sleeve 68 of control clamp 60 in order to change the flow cross section 72 so that the desired value of the dripping rate will be reached.

Upon removal of the protective cap 36 and insertion of the piercing tip 16 into the infusion flask the operator first adjusts a desired value which is indicated by the optical display means 24. The evaluation circuit 25 is so designed that, for example, no control will take place during the first five minutes of current supply (i.e. as of the removal of protective cap 36). This will give the operator sufficient time to adjust the desired value. It is only upon expiration of the predetermined period of time of, for example, five minutes, that the control clamp 60 will begin to regulate the flow rate to ±20% of the desired value. If these limit values are surpassed, a warning will be given by the display means 24, for example in that the signal indicated will begin to flash. It is also possible, to provide a separate source of sounding to give such warning.

The entire infusion device consisting of drip chamber 10, including the measuring and display means with the transmitter 26 and receiver 28, evaluation circuit 25, and display means 24, as well as the control clamp 60, including the drive motor 64 constitute one unit which permits the fully automatic indication and control of the dripping rate, including the balancing of any pressure variations at the patient end. The detailed description of the preferred embodiment of the invention having been set forth herein for the purpose of explaining the principles thereof, it is known that there may be modification, variation or change in the invention without departing from the proper scope of the invention and the claims thereto.

What is claimed is:

1. An infusion device comprising:
   an injection molded drip chamber for delivering a fluid having a lower part and an upper part having a drop outlet formed on an inner side thereof;
   drop sensing means formed on said upper part for sensing the passage of a drop of said fluid through said drop outlet of said drop chamber and producing a signal corresponding thereto;
   evaluation circuit means for receiving said signal from said drop sensing means;
   display means electrically connected to said evaluation circuit means for indicating a rate of said fluid delivery determined by said evaluation circuit means;
   a power source connected by electrical connection means to said evaluation circuit means and said display means for delivering operational power thereto; and
   a housing formed integrally with said upper part and extending outwardly from the circumference thereof for covering a small portion of the drip chamber relative to the total length of the drip chamber and having recesses formed therein for receiving said evaluation circuit, display means and power source.

2. The infusion device of claim 1, wherein the drop sensing means is a light barrier having optical transmission and receiving means electrically connected to said power source and said evaluation circuit means and the housing comprises two diametrically opposed arms projecting downwardly along opposite sides of the drip chamber and formed with recesses for receiving said optical transmission and receiving means.

3. The infusion device of claim 1 or 2 wherein said electrical connection means are wires formed in a wall of the housing.

4. The infusion device of claim 3 wherein the clamping jaws are arranged in approximately a circular sector shape perpendicular to a longtudinal axis of the hose.

5. The infusion device of claim 3 wherein the clamping jaws are displaceable along a plurality of differing radii extending from a longitudinal axis of the drip chamber by means of a rotating sleeve responsive to said drive means.

6. An infusion device comprising:
an injection molded drip chamber for delivering a fluid having a lower part and an upper part having a drop outlet formed on an inner side thereof;
drop sensing means formed on said upper part for sensing the passage of a drop of said fluid through said drop outlet of said drop chamber and producing a signal corresponding thereto;
evaluation circuit means for receiving said signal from said drop sensing means;
display means electrically connected to said evaluation circuit means for indicating a rate of said fluid delivery determined by said evaluation circuit means;
a power source connected by electrical connection means to said evaluation circuit means and said display means for delivering operational power thereto;
a housing formed integrally with said upper part and extending outwardly from the circumference thereof for covering a small portion of the drip chamber relative to the total length of the drip chamber and having recesses formed therein for receiving said evaluation circuit, display means and power source;
a piercing tip formed externally on an outer side of the upper part of the drip chamber; and
a protective cap for covering said piercing tip having an insulated disc portion for inhibiting said power source from delivering said operational power by interrupting the electrical connection thereto when said protective cap covers said piercing tip.

7. The infusion device in accordance with claims 1, 2, or 6 further comprising:
a control clamp for controlling the rate of flow through a hose connected at a lower end of the drip chamber by varying a cross-sectional flow area of said hose, said clamp having driving means responsive to said evaluation circuit means for controlling the relative position thereof.

8. The infusion device of claim 7 wherein said evaluation circuit means is a processor and said power source is a battery.

9. The infusion device of claims 7 wherein said control clamp comprises at least three clamping jaws of variable relative spacing for clamping the base therebetween.

* * * * *

UNITED STATES PATENT AND TRADEMARK OFFICE
CERTIFICATE OF CORRECTION

PATENT NO. : 4,775,368

DATED : October 4, 1988

INVENTOR(S) : Iwatschenko

It is certified that error appears in the above-identified patent and that said Letters Patent is hereby corrected as shown below:

First page, second column, following the third line, insert --FOREIGN PATENTS

| | | |
|---|---|---|
| 8,432,849 | Germany ---------- Jan. | 1985 |
| 8,516,066 | Germany ---------- Aug. | 1985 |
| 3,108,848 | Germany ---------- Jan. | 1982 |
| 3,408,572 | Germany ---------- Nov. | 1984 |
| 3,403,969 | Germany ---------- Aug. | 1985 |
| 154,163 | Germany ---------- Nov. | 1985 |
| 59,025 | Finland ---------- Feb. | 1938 |
| 18,817 | European --------- Nov. | 1980.--. |

Col. 1, line 29, delete "being";
line 45, after "measurement" delete "indicated".
Col. 3, line 66, "switch 5" should read --switch S,--.
Col. 5, line 30, "than" should read --that--.
Col. 6, line 63, "longtudinal" should be --longitudinal--.
Col. 8, line 21, "claims 7" should be --claim 7--.

Signed and Sealed this

Ninth Day of May, 1989

Attest:

DONALD J. QUIGG

*Attesting Officer*  *Commissioner of Patents and Trademarks*